United States Patent
Liao et al.

(10) Patent No.: US 6,645,955 B1
(45) Date of Patent: Nov. 11, 2003

(54) 3,6-DIHYDROXY-24-AMIDYL STEROID DERIVATIVES

(75) Inventors: Shutsung Liao, Chicago, IL (US); Ching Song, Chicago, IL (US)

(73) Assignee: Arch Development Corporation, Chicago, IL (US)

(*) Notice: Subject to any disclaimer, the term of this patent is extended or adjusted under 35 U.S.C. 154(b) by 0 days.

(21) Appl. No.: 09/560,236

(22) Filed: Apr. 28, 2000

Related U.S. Application Data

(60) Provisional application No. 60/131,728, filed on Apr. 30, 1999, and provisional application No. 60/191,864, filed on Mar. 24, 2000.

(51) Int. Cl.$^7$ .............................. A61K 31/56; C07J 9/00; C07J 41/00
(52) U.S. Cl. ......................... 514/182; 552/553; 552/554
(58) Field of Search ................... 514/182; 552/553, 552/554

(56) References Cited

U.S. PATENT DOCUMENTS

| | | | |
|---|---|---|---|
| 2,698,853 A | 1/1955 | Wildi | 260/397.2 |
| 4,125,544 A | 11/1978 | Dygos | 260/397.4 |
| 4,193,930 A | 3/1980 | Chorvat | 260/397.2 |
| 4,304,726 A | 12/1981 | Arakawa et al. | 260/397.2 |
| 4,917,898 A * | 4/1990 | Angelico et al. | 424/452 |
| 5,362,891 A * | 11/1994 | Bonaldi et al. | 552/554 |
| 5,424,463 A | 6/1995 | Lardy et al. | 552/637 |
| 5,466,815 A | 11/1995 | Enhsen et al. | 548/252 |
| 5,508,453 A | 4/1996 | Arosio et al. | 552/553 |
| 5,562,910 A | 10/1996 | Daynes et al. | 424/278.1 |
| 5,583,239 A * | 12/1996 | Regen | 552/554 |
| 5,639,744 A | 6/1997 | Marchi et al. | 514/176 |
| 6,060,465 A * | 5/2000 | Miljkovic et al. | 514/169 |
| 6,369,247 B1 | 9/2002 | Miller et al. | 552/542 |

FOREIGN PATENT DOCUMENTS

| | | |
|---|---|---|
| CN | 1100729 | 3/1995 |
| JP | 4169597 | * 6/1992 |
| WO | WO 94/02503 | * 2/1994 |
| WO | 9832444 | 7/1998 |

OTHER PUBLICATIONS

Fini et al., J. Pharm. Sci., vol. 79(7), pp. 603–605, 1990.*

Cohen et al., "The preparation of bile acid amides and oxazolines. II. The synthesis of the amides and oxazolines of ursodeoxycholic acid, deoxycholic acid, hydeoxycholic acid and cholic acid.", Steroids, vol. 40(6), Dec. 1982, pp. 701–711.*

Angelico et al., Dissolution of Human Cholesterol Gallstones in Bile Salt/Lecithin Mixtures: Effect of Bile Salt Hydrophobicity and Various pHs, Scandinavian Journal of Gasteroenterology 30:1178–1185, 1995.

Coleman et al., "Synthesis and Characterization of Novel Analogs of Conjugated Bile Acids Containing Reversed Amide Bonds", Journal of Lipid Research 36:901–910, 1995.

Janowski et al., "Structural Requirements of Ligands for the Oxysterol Liver X Receptors LXRα and LXRβ", Proc. Natl. Acad. Sci. 96:266–271, 1999.

Kim et al., "Inhibitors of Sterol Synthesis. Chemical Synthesis, Structure, and Biological Activities of (25R)–3β, 26–dihydroxy–5αcholest–8(14)–en–15–one, a Metabolite of 3β–hydroxy–5α–cholest–8(14)–en–15–one", Journal of Lipid Research 30:247–261, 1989.

Kurosawa et al., "Synthesis of 3α, 7α, 12α–trihydroxy–and 3α, 7α–dihydroxy–5β–cholestan–26–oic Acids by the Use of β–ketosulfoxide", Steroids 60:439–444, 1995.

Li et al., "Sterol Synthesis. Preparation and Characterization of Fluorinated and Deuterated Analogs of Oxygenated Derivatives of Cholesterol", Chemistry and Physics of Lipids 99:33–71, 1999.

Roda et al., "Synthesis and Phsicochemical, Biological, and Pharmacological Properties of New Bile Acids Amidated with Cyclic Amino Acids", J. Med. Chem. 39:2270–2276, 1996.

Ruelle et al., "The Mobile Order Solubility Equation Applied to Polyfunctional Molecules: The Non–hydroxysteroids in Aqueous and NonAqueous solvents", International Journal of Pharmaceutics 157:219–232, 1997.

Song et al., "Ubiquitous Receptor: A Receptor that Modulates Gene Activation by Retinoic Acid and Thyroid Hormone Receptors", Proc. Natl. Acad. Sci. 91:10809–10813, 1994.

Song et al., "Ubiquitous Receptor: Structures, Immunocytochemical Localization, and Modulation of Gene Activation by Receptors for Retinoic Acids and Thyroid Hormones", Annals of the New York Academy of Sciences 761:38–49, 1995.

Sweeny et al., "Metabolism of 5–fluorouracil to an N–cholyl–2–fluro–β–alanine conjugate: Previously Unrecognized Role for Bile Acids in Drug Conjugation", Proc. Natl. Acad. Sci. 84:5439–5443, 1987.

Summerfield et al., "Indentification of Bile Acids in the Serum and Urine in Cholestasis", Biochem. J. 154:507–516, 1976.

Varma et al., "Synthesis and C–25 Chirality of26–Hydroxycholesterols", The Journal of Organic Chemistry 40:3680–3686, 1975.

Wei et al., "Modulation of Hormone–dependent Glucocorticoid Receptor Function Using a Tetracycline–regulated Expression System", J. Steroid Biochem. Molec. Biol. 64:1–12, 1998.

Xia et al., "Synthesis of N–Substituted 3–OXO–17β–Carboxamide–4–AZA–5α–Androstanes and the Tautromerism of 3–OXO–4–AZA–5–Androstenes", Heterocycles 47:703–716, 1998.

(List continued on next page.)

*Primary Examiner*—Barbara P. Badio
(74) *Attorney, Agent, or Firm*—Fish & Richardson P.C.

(57) ABSTRACT

Steroid derivatives of this invention interact with nuclear liver X receptor (LXR) and ubiquitous receptor (UR) and can be used to treat a variety of LXR- or UR-mediated disorders.

13 Claims, No Drawings-

OTHER PUBLICATIONS

Josef E. Herz, et al., "Fluorinated Sterols. Part II: 26,27—Polyfluorinated Desmosterols", *Journal of Fluorine Chemistry*, vol. 8, pp. 209–222 (1976).

Mohammed N. Iqbal, et al., "Bile Acids. LXXXI. Synthesis and structural assignment of E/Z isomers of substituted methyl hydroxy–5β–cholest–24–en–26–oates", *Steroids*, vol. 56, pp. 505–512 (Oct., 1991).

Naoyuki Koizumi, et al., Synthesis of [25R]—and [25S]25,26–Dihydroxyvitamin D31, *Tetrahedron Letters*, No. 32, pp. 2899–2902 (1978).

Dieter Leibfritz, et al., "Nuclear Magnetic Resonance Spectroscopy. Carbon–13 Spectra of Cholic Acids and Hydrocarbons Included in Sodium Desoxycholate Solutions", *Journal of American Chemical Society*, vol. 95, No. 14, pp. 4996–5003 (Jul. 11, 1973).

S.H. Mujtaba Naqvi, "Chemical Synthesis and Mass Spectrometric Characterization of Some C–27 Steroids", *Steroids*, vol. 22, pp. 285–290 (1973).

Stephen A. Ziller, Jr., et al., "Bile Acids. XXV. Allochenodeoycholic Acid, A Metabolite of 5α–Cholestan–3β–OL in the Hyperthyroid Rat", *The Journal of Biological Chemistry*, vol. 243, pp. 5280–5288 (1968).

Bleau et al., "Cholesterol sulfate. I. Occurrence and possible biological function as an amphipathic lipid in the membrane of the human erythrocyte." *Biochimica et Biophysica Acta*, vol. 352(1), pp. 1–9, (1974).

Dusza et al., "A Fusion Method for Preparation of Steriod Sulfates," Steroids pp. 317–323 (1985).

Dusza et al., "The Preparation of Estradiol–17β Sulfates with Triethylamine–Sulfur Trioxide," Steroids pp. 303–315 (1985).

Charles Freudenreich, et al., "Design of Inhibitors from the Three–Dimensional Structure of Alcohol Dehydrogenase, Chemical Synthesis and Enzymatic Properties", *J. Am. Chem. Soc.*, pp. 3344–3353, (1984).

Bethany A. Janowski, et al., "Structural requirements of ligands for the oxysterol liver X receptors LXRa and LXRb,"Proc. Nat.. Acad. Sci., USA, vol. 96, pp. 266–271, (Jan. 1999).

Kornel et al., "Studies on Steroid Conjugates: II Chemical Synthesis and Characterization of Sodium Cortisol–21–Sulfate and Sodium Tetrahydrocortisol–3, 21–Disulfate," Steroids. pp. 67–75 (1964).

Nambara et al., "Preparation of Specific Antiserum to Estriol 3–Sulfate 16–Glucuronide," Journal of Steriod Biochemistry, *21*: pp. 199–203 (1984).

Tanaka et al., "Specific Antisera for the Radioimmunoassay of Estradiol–3–Sulfate," Journal of Steroid Biochemistry, 22: pp. 285–288 (1985).

Database HPCAPLUS, An 1974:461503, Bleau, G. et al. Cholesterol Sulfate, Occurrence and possible biological function as an amphipathic lipid in the membrane of the human erythrocyte. Biochim, Biophys, Acta, Jan. 1974, vol. 352, No. 1, pp. 1–9.

Runong Wang et al., "Chemical Product Manual", the third version, Pharmaceuticals, chemical Industry Publishing House, p. 740 (Jan. 1999).

* cited by examiner

3,6-DIHYDROXY-24-AMIDYL STEROID DERIVATIVES

CROSS-REFERENCE TO RELATED APPLICATIONS

Pursuant to 35 USC §119(e), this application claims the benefit of prior U.S. provisional applications No. 60/131,728, filed Apr. 30, 1999; and No. 60/191,864, filed Mar. 24, 2000.

STATEMENT AS TO FEDERALLY SPONSORED RESEARCH

This invention was made with Government support under NIH CA 58073 from National Institute of Health. The Government may have certain rights in this invention.

BACKGROUND

Nuclear receptors are a family of transcription factors modulated by small hydrophobic signaling molecules, like steroids, thyroid hormone, free fatty acids, vitamin D and retinoids. Nuclear receptors are important pharmacological targets for drug intervention in disease management. For example, Tamoxifen, an estrogen antagonist, interacts with estrogen receptor to deliver its therapeutic effects on breast cancer; RU486, an antagonist of progesterone receptor, is used for termination of pregnancies and menopause-related disorders; and Dexamethasone interacts with glucocorticoid receptor to suppress immune system function and is useful for treating inflammatory diseases such as asthma.

Nuclear receptors have three independent domains I, II and III. Domains I and III modulate transcriptional activities by interacting with other factors of the transcription complex; Domain II involves in DNA-binding; and Domain III is the ligand-binding domain. Domain II is the most conserved region within the nuclear receptor family, with a unique feature of four pairs of cysteine chelated with two zinc atoms which form a "zinc finger" structure. The three domains of nuclear receptors are functionally interchangeable between different members. For example, the androgen receptor DNA-binding domain can be fused to the ligand-binding domain of estrogen receptor and the resulting AR-ER chimeric receptor can modulate androgen-responsive genes by binding to estrogen.

Amino acid sequence homology of the DNA-binding domain between members of nuclear receptor family allows identification of new members of this family through low stringency nucleotide-probe screening. Human genome project also facilitates identification of new genes coding for new nuclear receptors. At present, a few dozens of nuclear receptors have been identified and sequenced, but their ligands have yet to be identified. Recently, a novel nuclear receptor was cloned through degenerate oligonucleotide screening from human and rat cells and was named ubiquitous nuclear receptor ("UR"), because of its ubiquitous expression pattern in the body. UR has been found to form heterodimers with RXR receptors and binds to double-stranded DNA with the sequence motif: AGGTCANNNNAGGTCA (SEQ ID NO: 1) ("DR4"). Promoters containing DR4 can be activated by UR and RXR heterodimer in cultured cells.

LXRa, another new member of the nuclear receptor family has been cloned recently. Amino acid sequence analysis revealed that it shares over 80% homology with UR in the DNA- and ligand-binding domain. The expression of LXRa mRNA is limited to liver and a few other tissues. LXRa has been identified as a transcriptional activator of the cholesterol 7α-hydroxylase gene and plays an important role in cholesterol catabolism.

Recently other nuclear proteins interacting with nuclear receptors have been identified through yeast two-hybrid screening techniques, among which are co-activators and co-repressors of nuclear receptors, e.g., SRC1, 2, 3, and Grip1. These proteins interact with nuclear receptors in a ligand-dependent manner. This property is useful to set up biochemical assays for ligand-receptor interaction.

Steroid derivatives described in this invention are found to modulate the transcriptional activities via binding to UR or LXRa, and thus can be used to treat disorders mediated by such receptors such as atherosclerosis.

SUMMARY

An aspect of this invention relates to steroid derivatives of formula (I):

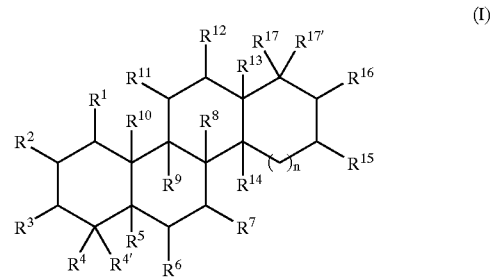

$R^3$ is hydrogen, amino, carboxyl, oxo, halo, sulfonic acid, —O-sulfonic acid, or alkyl that is optionally inserted with —NH—, —N(alkyl)-, —O—, —S—, —SO—, —SO$_2$—, —O—SO$_2$—, —SO$_2$—O—, —O—SO$_3$—, —SO$_3$—O—, —CO—, —CO—O—, —O—CO—, —CO—NH—, —CO—N(alkyl)-, —NH—CO—, or —N(alkyl)-CO—, and further optionally substituted with hydroxy, halo, amino, carboxyl, sulfonic acid, or —O—0 sulfonic acid. Each of $R^1$, $R^2$, $R^4$, $R^{4'}$, $R^6$, $R^7$, $R^{11}$, $R^{12}$, $R^{15}$, $R^{16}$ and $R^{17'}$, independently, is hydrogen, hydroxy, amino, carboxyl, oxo, halo, sulfonic acid, —O-sulfonic acid, or alkyl that is optionally inserted with —NH—, —N(alkyl)-, —O—, —S—, —SO—, —SO$_2$—, —O—SO$_2$—, —SO$_2$—O—, —O—SO$_3$—, —SO$_3$—O—, —CO—, —CO—O—, —O—CO—, —CO—NH—, —CO—N(alkyl)-, —NH—CO—, or —N(alkyl)-CO—, and further optionally substituted with hydroxy, halo, amino, carboxyl, sulfonic acid, or —O-sulfonic acid. Each of $R^5$, $R^8$, $R^9$, $R^{10}$, $R^{13}$, and $R^{14}$, independently, is hydrogen, alkyl, haloalkyl, hydroxyalkyl, alkoxy, hydroxy, or amino. $R^{17}$ is —X—Y—Z. X is a bond, or alkyl or alkenyl, optionally inserted with —NH—, —N(alkyl)-, —O—, or —S—, and further optionally forming a cyclic moiety with $R^{16}$ and the 2 ring carbon atoms to which $R^{16}$ and $R^{17}$ are bonded. Y is —CO—, —SO—, —SO$_2$—, —O—SO$_2$—, —SO$_2$—O—, —O—SO$_3$—, —SO$_3$—O—, —CO—O—, —O—CO—, —CO—NH—, —CO—N(alkyl)-, —NH—CO—, —N(alkyl)-CO—, or a bond. Z is alkyl, alkenyl, alkynyl, cycloalkyl, heterocycloalkyl, cycloalkenyl, heterocycloalkenyl, aryl, heteroaryl, aralkyl, or heteroaralkyl, and is optionally substituted with hydroxy, alkoxy, amino, halo, sulfonic acid, —O-sulfonic acid, carboxyl, oxo, alkyloxycarbonyl, alkylcarbonyloxy, alkylaminocarbonyl, alkylcarbonylamino, alkylcarbonyl, alkylsulfinyl, alkylsulfonyl, or alkylthio; or is —CH(A)—B. A being a side chain of an amino acid, and B is hydrogen, —NR$^a$R$^b$, or —COOR$^c$ wherein each of R$^a$, R$^b$, and R$^c$, independently, is hydrogen or alkyl. n is 0, 1, or 2. Note that when Z is substituted with carboxyl or alkyloxycarbonyl, Y is a bond and either X or Z contains at least one double bond, and that when Y is a bond, either X is —NH-alkyl-, —NH-alkenyl-, —N(alkyl)-alkyl-, —N(alkyl)-alkenyl-, —O-alkyl-, —O-alkenyl-, —S-alkyl-, or —S-alkenyl-; or Z is substituted with halo, sulfonic acid, —O-sulfonic acid, alkylsulfinyl, or alkylsulfonyl, or is alkenyl.

Another aspect of this invention relates to steroid derivatives having the formula (I) as depicted above. Each of R$^1$, R$^2$, R$^3$, R$^4$, R$^{4'}$, R$^6$, R$^7$, R$^{11}$, R$^{12}$, R$^{15}$, R$^{16}$, and R$^{17'}$, independently, is hydrogen, hydroxy, amino, carboxyl, oxo, halo, sulfonic acid, —O-sulfonic acid, or alkyl that is optionally inserted with —NH—, —N(alkyl)-, —O—, —S—, —SO—, —SO$_2$—, —O—SO$_2$—, —SO$_2$—O—, —O—SO$_3$—, —SO$_3$—O—, —CO—, —CO—O—, —O—CO—, —CO—NH—, —CO—N(alkyl)-, —NH—CO—, or —N(alkyl)-CO—, and further optionally substituted with hydroxy, halo, amino, carboxyl, sulfonic acid, or —O-sulfonic acid. Each of R$^5$, R$^8$, R$^9$, R$^{10}$, R$^{13}$, and R$^{14}$, independently, is hydrogen, alkyl, haloalkyl, hydroxyalkyl, alkoxy, hydroxy, or amino. R$^{17}$ is —X—Y—Z. X is a bond, or alkyl or alkenyl, optionally inserted with —NH—, —N(alkyl)-, —O—, or —S—, and further optionally forming a cyclic moiety with R$^{16}$ and the 2 ring carbon atoms to which R$^{16}$ and R$^{17}$ are bonded. Y is —CO—, —SO—, —SO$_2$—, —O—SO$_2$—, —SO$_2$—O—, —O—SO$_3$—, —SO$_3$—O—, —CO—O—, —O—CO—, —CO—NH—, —CO—N(alkyl)-, —NH—CO—, —N(alkyl)—CO-, or a bond. Z is alkyl, alkenyl, alkynyl, cycloalkyl, heterocycloalkyl, cycloalkenyl, heterocycloalkenyl, aryl, heteroaryl, aralkyl, or heteroaralkyl, and is optionally substituted with hydroxy, alkoxy, amino, halo, sulfonic acid, —O-sulfonic acid, carboxyl, oxo, alkyloxycarbonyl, alkylcarbonyloxy, alkylaminocarbonyl, alkylcarbonylamino, alkylcarbonyl, alkylsulfinyl, alkylsulfonyl, or alkylthio; or is —CH(A)—B. A is an amino acid side chain containing an aromatic moiety, and B is hydrogen, —NR$^a$R$^b$, or —COOR$^c$ wherein each of R$^a$, R$^b$, and R$^c$, independently, is hydrogen or alkyl. n is 0, 1, or 2. Note that when Z is substituted with carboxyl or alkyloxycarbonyl, Y is a bond and either X or Z contains at least one double bond, and that when Y is a bond, either X is —NH-alkyl-, —NH-alkenyl-, —N(alkyl)-alkyl-, —N(alkyl)-alkenyl-, —O-alkyl-, —O-alkenyl-, —S-alkyl-, or —S-alkenyl-; or Z is substituted with halo, sulfonic acid, —O-sulfonic acid, alkylsulfinyl, or alkylsulfonyl, or is alkenyl.

A further aspect of this invention relates to steroid derivatives of formula (I), supra. Each of R$^1$, R$^2$, R$^3$, R$^4$, R$^{4'}$, R$^6$, R$^7$, R$^{11}$, R$^{12}$, R$^{15}$, R$^{16}$, and R$^{17'}$, independently, is hydrogen, hydroxy, amino, carboxyl, oxo, halo, sulfonic acid, —O-sulfonic acid, or alkyl optionally inserted with —NH—, —N(alkyl)-, —O—, —S—, —SO—, —SO$_2$—, —O—SO$_2$—, —SO$_2$—O—, —O—SO$_3$—, —SO$_3$—O—, —CO—, —CO—O—, —O—CO—, —CO—NH—, —CO—N(alkyl)-, —NH—CO—, or —N(alkyl)-CO—, and further optionally substituted with hydroxy, halo, amino, carboxyl, sulfonic acid, or —O-sulfonic acid. Each of R$^5$, R$^8$, R$^9$, R$^{10}$, R$^{13}$, and R$^{14}$, independently, is hydrogen, alkyl, haloalkyl, hydroxyalkyl, alkoxy, hydroxy, or amino. R$^{17}$ is —X—Y—Z. X is a bond, or alkyl or alkenyl, optionally inserted with —NH—, —N(alkyl)-, —O—, or —S—, and further optionally forming a cyclic moiety with R$^{16}$ and the 2 ring carbon atoms to which R$^{16}$ and R$^{17}$ are bonded. Y is —CO—, —SO—, —SO$_2$—, —O—SO$_2$—, —SO$_2$—O—, —O—SO$_3$—, —SO$_3$—O—, —CO—O—, —O—CO—, —CO—NH—, —CO—N(alkyl)-, —NH—CO—, —N(alkyl)-CO—, or a bond. Z is alkyl, alkenyl, alkynyl, cycloalkyl, heterocycloalkyl, cycloalkenyl, heterocycloalkenyl, aryl, heteroaryl, aralkyl, or heteroaralkyl, and is optionally substituted with hydroxy, alkoxy, amino, halo, sulfonic acid, —O-sulfonic acid, carboxyl, oxo, alkyloxycarbonyl, alkylcarbonyloxy, alkylaminocarbonyl, alkylcarbonylamino, alkylcarbonyl, alkylsulfinyl, alkylsulfonyl, or alkylthio; or is —CH(A)—B. A is a side chain of an amino acid, and B is hydrogen, —NR$^a$R$^b$, or —COOR$^c$ wherein each of R$^a$, R$^b$, and R$^c$, independently, is hydrogen or alkyl. n is 0, 1, or 2. Note that when Z is substituted with carboxyl or alkyloxycarbonyl, Y is a bond and either X or Z contains at least one double bond, and that when Y is a bond, either X is —NH-alkyl-, —NH-alkenyl-, —N(alkyl)-alkyl-, —N(alkyl)-alkenyl-, —O-alkyl-, —O-alkenyl-, —S-alkyl-, or —S-alkenyl-; or Z is substituted with halo, sulfonic acid, —O-sulfonic acid, alkylsulfinyl, or alkylsulfonyl, or is alkenyl; and that at least one of R$^3$ and R$^4$, R$^4$ and R$^5$, R$^5$ and R$^6$, R$^7$ and R$^8$, R$^{12}$ and R$^{13}$, and R$^{15}$ and R$^{16}$ independently, is deleted to form a double bond. One subset of the just-described steroid derivatives encompasses compounds which are featured by the presence of at least one double bond in the rings, which are formed by deleting one or more of the following pairs of substituents: R$^3$ and R$^4$, R$^4$ and R$^5$, R$^{12}$ and R$^{13}$, and R$^{15}$ and R$^{16}$. Another subset encompasses compounds which are featured by that Z is alkenyl, alkynyl, cycloalkyl, heterocycloalkyl, cycloalkenyl, heterocycloalkenyl, aryl, heteroaryl, aralkyl, or heteroaralkyl, and optionally substituted with hydroxy, alkoxy, amino, or halo; or is —CH(A)—B. A and B are as described above.

Note that X and Z optionally join together to form a cyclic moiety. For example, if both X and Z are alkyl, and Y is —C(=O)—O—, a lactone results from joining X and Z.

A salt of the steroid derivative of this invention is also within the scope of this invention and can be formed, for example, between the steroid of this invention having a carboxylate and a cationic counterion such as an alkali metal cation, e.g., a sodium ion or a potassium ion; or an ammonium cation that can be substituted with organic groups, e.g., a tetramethylammonium ion or a diisopropylethylammonium ion. A salt of this invention can also form between the steroid derivative of this invention having a protonated amino group and an anionic counterion, e.g., a sulfate ion, a nitrate ion, a phosphate ion, or an acetate ion.

Set forth below are some examples of steroid derivatives of this invention:

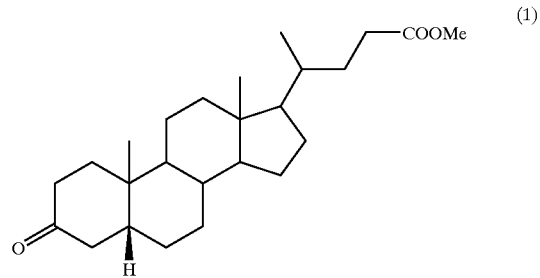

(2)
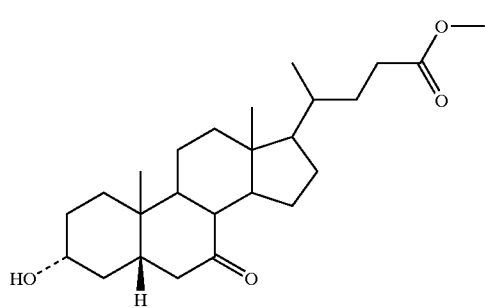
(3)
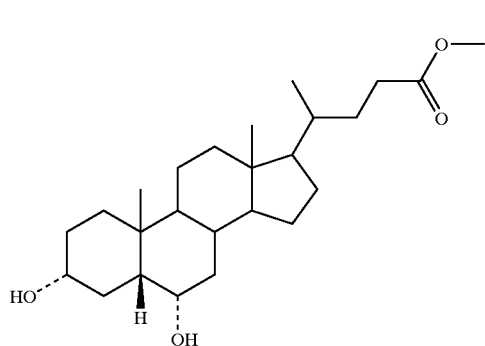
(4)
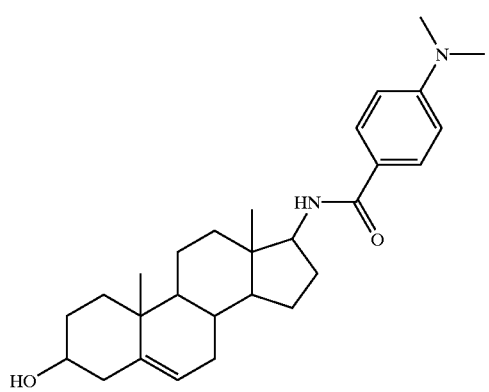
(5)
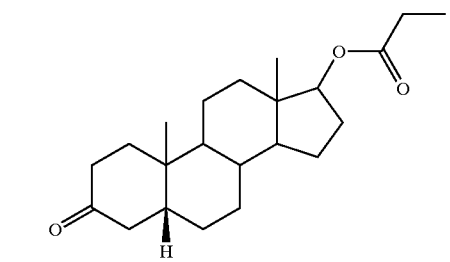
(6)
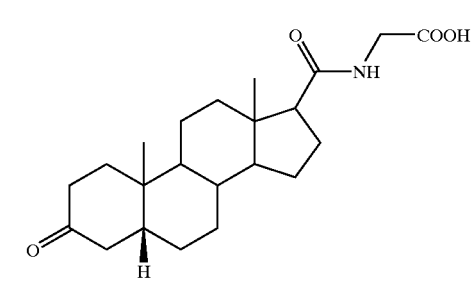
(7)
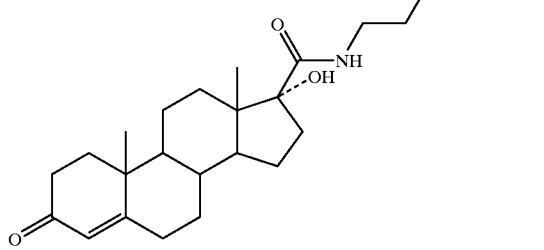
(8)
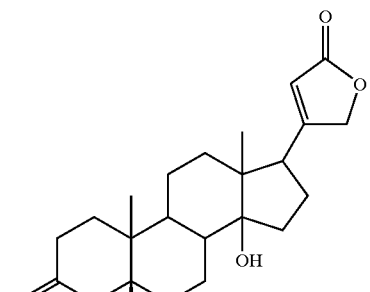
(9)
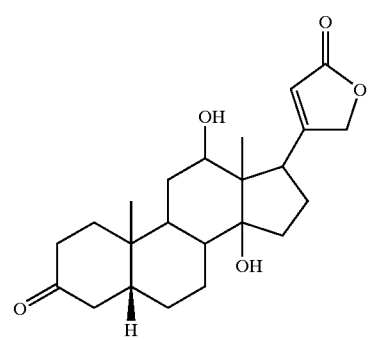
(10)
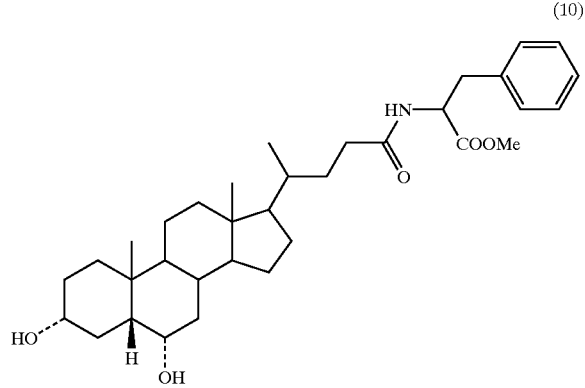

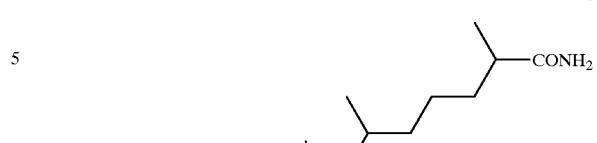
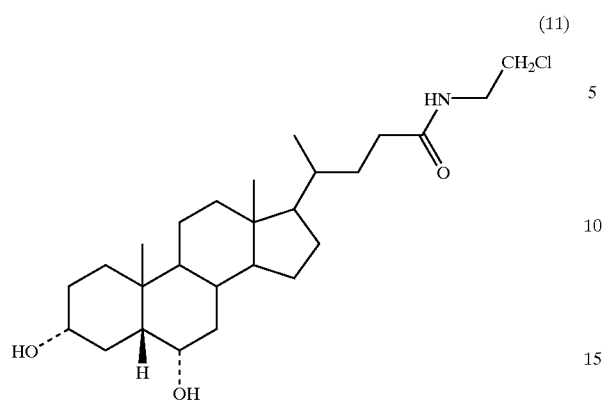
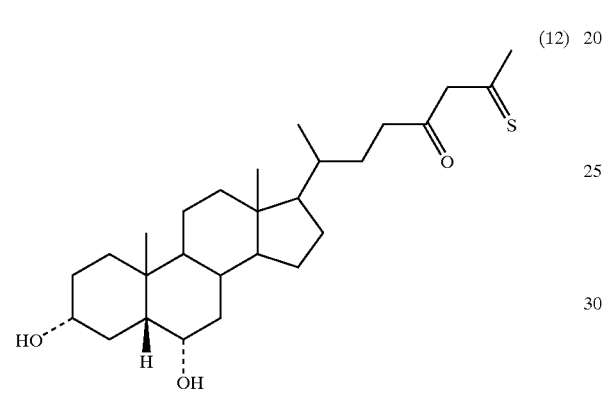
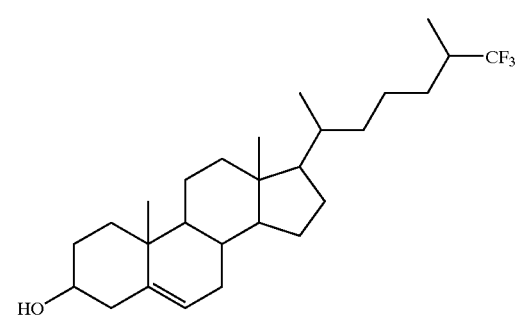
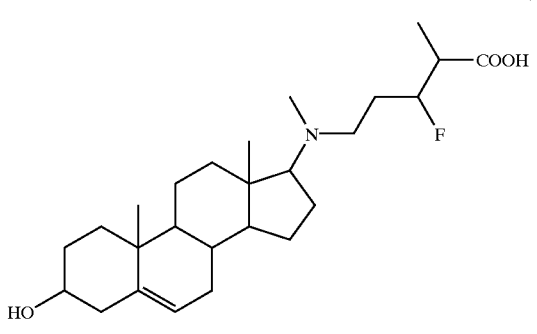

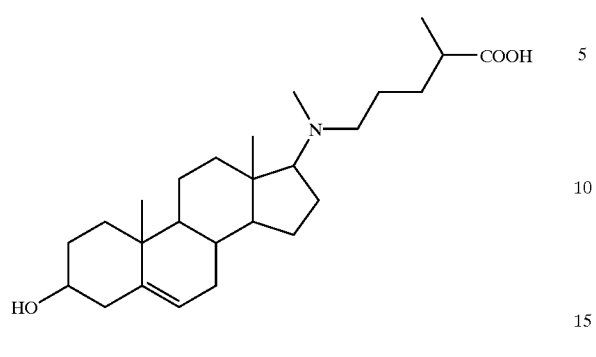
(19)
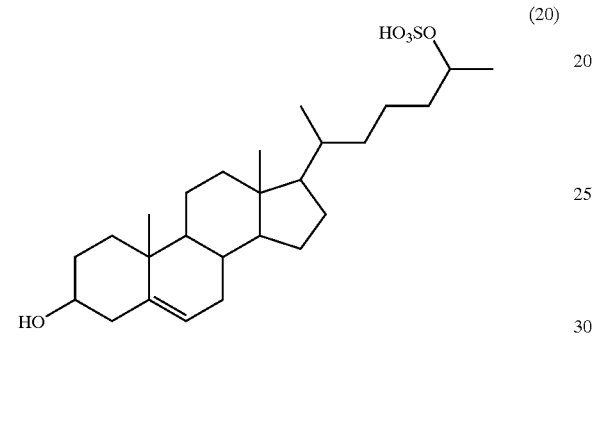
(20)
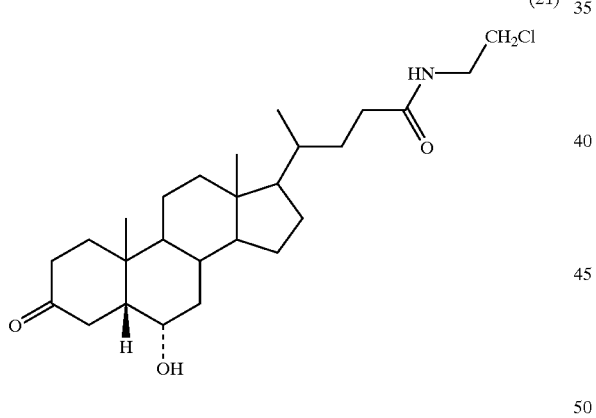
(21)
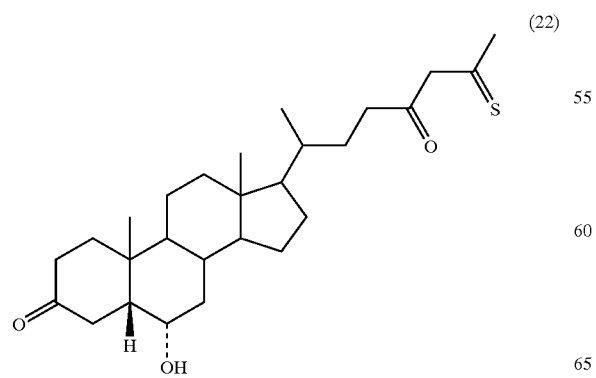
(22)
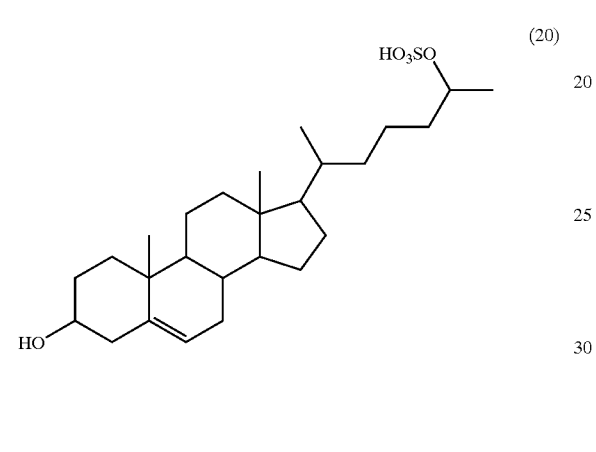
(23)
(24)
(25)
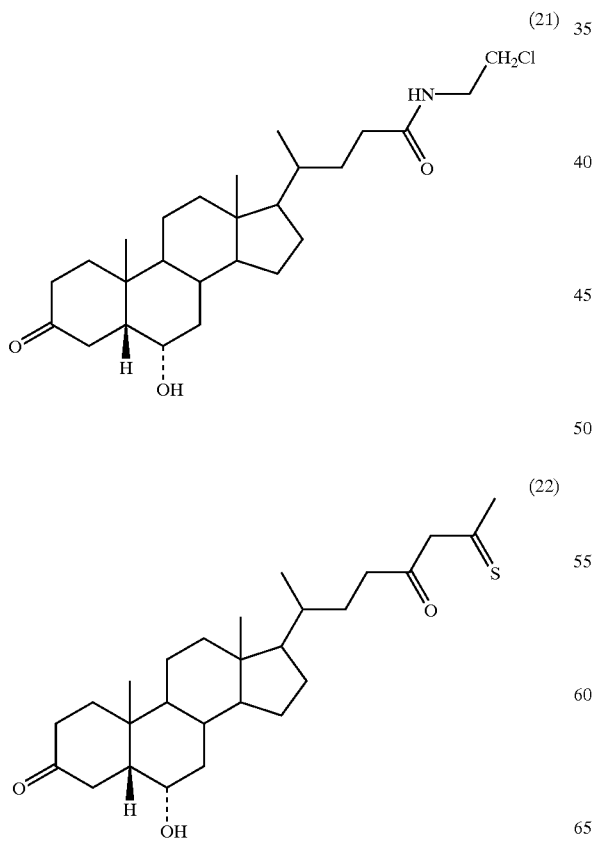
(26)

-continued

(27)
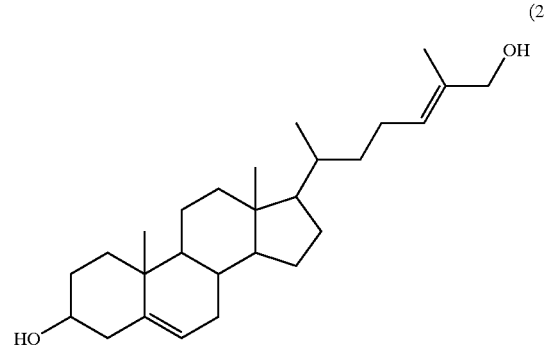

(28)
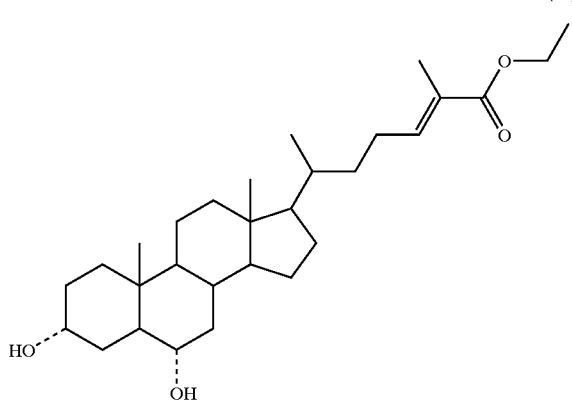

(29)
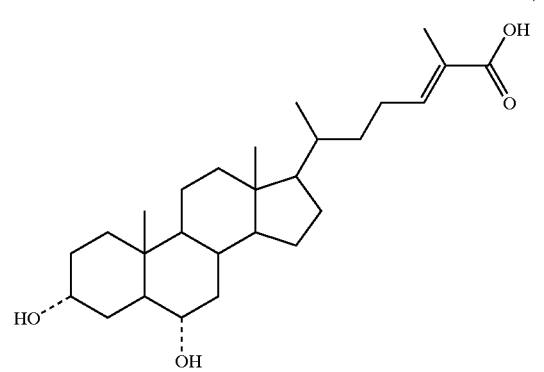

(30)
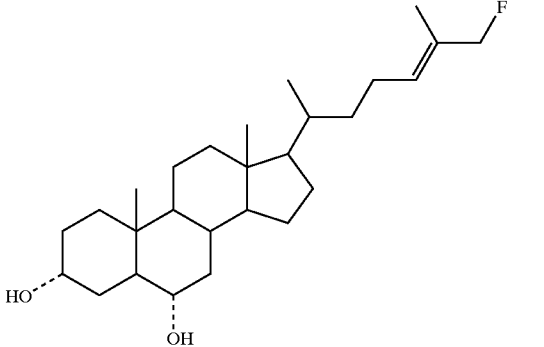
and

-continued

(31)
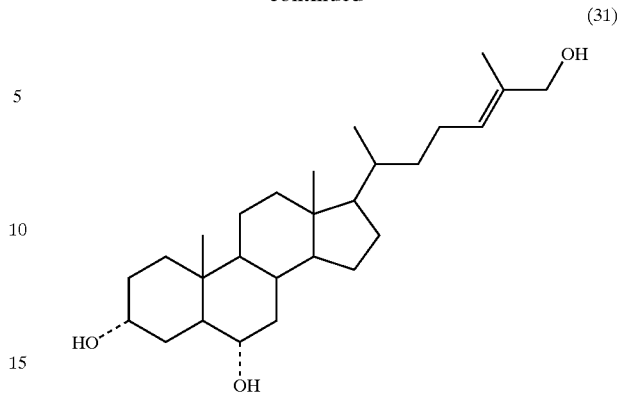

As used herein, the term "alkyl" in this disclosure denotes a straight or branched hydrocarbon chain containing 1–8 carbon atoms. Some examples of an alkyl group are methyl, ethyl, propyl, isopropyl, butyl, isobutyl, tert-butyl, pentyl, hexyl, heptyl, octyl, or 2-methylpentyl. By the term "cycloalkyl" is meant a cyclic hydrocarbon chain that has 3–8 carbon atoms. The cycloalkyl groups herein described may also contain fused rings. Fused rings are rings that share a common carbon-carbon bond. Examples of cycloalkyl groups include, but not limited to, cyclopropyl, cyclopentyl, cyclohexyl, cycloheptyl, adamantyl, and norbornyl.

The term "alkenyl" refers to a straight or branched hydrocarbon chain containing 2–8 carbon atoms and characterized in having one or more double bonds. Examples of a typical alkenyl include, but not limited to, allyl, propenyl, 2-butenyl, 3-hexenyl and 3-octenyl groups. The term "cycloalkenyl" is meant a cyclic hydrocarbon chain containing 3–8 carbon atoms and having at least one or more double bonds. Similar to the definition of cycloalkyl groups above, cycloalkenyl groups may also contain fused rings. Some examples of cycloalkenyl groups are cyclopentenyl, cyclohexenyl, cycloheptenyl, norbornylenyl, and cyclooctenyl groups.

The term "alkynyl" refers to a straight or branched hydrocarbon chain containing 2–8 carbon atoms and characterized in having one or more triple bonds. Some examples of a typical alkynyl are ethynyl, 2-propynyl, and 3-methylbutynyl.

The terms "heterocycloalkyl" and "heterocycloalkenyl" refer to cycloalkyl and cycloalkenyl groups which contain one or more heteroatoms, such as, nitrogen, oxygen, or sulfur. Typical heterocycloalkyl and heterocycloalkenyl groups include tetrahydrofuranyl, tetrahydropyranyl, piperidinyl, morpholino, pyrrolinyl and pyrrolidinyl.

"Aryl" represents an aromatic moiety which contains 6–12 carbon atoms and can contain fused rings. A fused ring is an aromatic group which contains at least two aryl rings sharing a common carbon-carbon bond. Typical examples of aryl include phenyl and naphthyl.

"Heteroaryl" groups in this disclosure are aromatic groups containing 5 to 12 ring atoms, in which one or more of these ring atoms are heteroatoms as defined above. Some examples of heteroaryl groups are pyridyl, pyrazinyl, furyl, pyrrolyl, thienyl, thiazolyl, benzimidazolyl, and imidazolyl.

The positions of substituents on each of the cyclic groups described herein may be at any available position, unless specified otherwise. For example, a methyl substituent on a benzene ring can be attached at the ortho, meta, or para position.

The term "alkoxy" is defined as the moiety "—O-alkyl." Some examples are methoxy, ethoxy, propoxy, isopropoxy, and t-butoxy. "Halo" represents a halogen atom, such as, fluoro, chloro, bromo, or iodo. By the terms "haloalkyl" and "hydroxyalkyl" are meant alkyl groups which are respectively substituted with one or more halogen atoms and one or more hydroxy groups. The nitrogen atom in an amino or amido group present in a steroid derivative of this invention can be mono- or di-substituted with an alkyl, a cycloalkyl, a heterocycloalkyl, an aryl, or a heteroaryl.

For convenience, a divalent moiety is named herein as if it were a monovalent moiety. For example, "alkyl," such as $CH_3$, which is assigned to X, actually stands for "alkylene," such as —$CH_2$—. As recognized by a skilled person in the art, steroid derivatives described herein contain stereocenters. Both the racemic mixtures of isomers and the optically pure isomers are within the scope of this invention.

Yet another aspect of this invention relates to a pharmaceutical composition for treating a UR- or LXRa-mediated disorder which contains a pharmaceutically acceptable carrier and an effective amount of one or more of the steroid derivatives described above. The use of such a steroid derivative or a salt thereof for the manufacture of a medicament for treating the above-mentioned disorders is also within the scope of this invention.

A still further aspect of this invention relates to a pharmacological composition for treating cancer, including solid tumors and leukemia, and immune dysfunction. The pharmacological composition contains a pharmaceutically acceptable carrier and an effective amount of one or more of a steroid derivative of formula (I), supra. Each of $R^1$, $R^2$, $R^3$, $R^4$, $R^{4'}$, $R^6$, $R^7$, $R^{11}$, $R^{12}$, $R^{15}$, $R^{16}$, and $R^{17}$, independently, is hydrogen, hydroxy, amino, carboxyl, oxo, halo, sulfonic acid, —O-sulfonic acid, or alkyl that is optionally inserted with —NH—, —N(alkyl)-, —O—, —S—, —SO—, —$SO_2$—, —O—$SO_2$—, —$SO_2$—O—, —O—$SO_3$—, —$SO_3$—O—, —CO—, —CO—O—, —O—CO—, —CO—NH—, —CO—N(alkyl)-, —NH—CO—, or —N(alkyl)-CO—, and further optionally substituted with hydroxy, halo, amino, carboxyl, sulfonic acid, or —O-sulfonic acid. Each of $R^5$, $R^8$, $R^9$, $R^{10}$, $R^{13}$, and $R^{14}$, independently, is hydrogen, alkyl, haloalkyl, hydroxyalkyl, alkoxy, hydroxy, or amino. $R^{17}$ is —X—Y—Z, in which X is a bond, or alkyl or alkenyl, optionally inserted with —NH—, —N(alkyl)-, —O—, or —S—, and further optionally forming a cyclic moiety with $R^{16}$ and the 2 ring carbon atoms to which $R^{16}$ and R are bonded; Y is —CO—, —SO—, —$SO_2$—, —O—$SO_2$—, —$SO_2$—O—, —O—$SO_3$—, —$SO_3$—O—, —CO—O—, —O—CO—, —CO—NH—, —CO—N(alkyl)-, —NH—CO—, —N(alkyl)-CO—, or a bond; and Z is alkyl, alkenyl, alkynyl, cycloalkyl, heterocycloalkyl, cycloalkenyl, heterocycloalkenyl, aryl, heteroaryl, aralkyl, or heteroaralkyl, and is optionally substituted with hydroxy, alkoxy, amino, halo, sulfonic acid, —O-sulfonic acid, carboxyl, alkyloxycarbonyl, alkylcarbonyloxy, alkylaminocarbonyl, alkylcarbonylamino, alkylcarbonyl, alkylsulfinyl, alkylsulfonyl, or alkylthio; or is —CH(A)—B with A being a side chain of an amino acid, and B being hydrogen, $NR^aR^b$, or —$COOR^c$ wherein each of $R^a$, $R^b$, and $R^c$, independently, is hydrogen or alkyl; and n is 0, 1, or 2. When Z is substituted with carboxyl, Y is a bond and either X or Z contains at least one double bond, and when Y is a bond, either X is —NH-alkyl-, —NH-alkenyl-, —N(alkyl)-alkyl-, —N(alkyl)-alkenyl-, —O-alkyl-, —O-alkenyl-, —S-alkyl-, or —S-alkenyl-; or Z is substituted with halo, sulfonic acid, —O-sulfonic acid, alkylsulfinyl, or alkylsulfonyl, or is alkenyl. The use of a just-described steroid derivative or a salt thereof for the manufacture of a medicament for treating the above-mentioned disorders is also within the scope of this invention.

Still another aspect of the present invention relates to a method of treating a UR- or LXRa-mediated disorder by administering to a patient in need thereof an effective amount of one of the pharmaceutical compositions decribed above. Some examples of UR- or LXRa-mediated disorders are: liver cirrhosis, gallstone disease, hyperlipoproteinemias, Alzheimer's disease, anemia, chronic inflammatory diseases (e.g., rheumatoid arthritis), metabolic disorders (e.g., diabetes), and cancers which are associated with UR expression, e.g., breast cancer, colon cancer, prostate cancer, and leukemia. Patients with other disorders such as atherosclerosis and liver cholestasis can also be treated with one of the pharmaceutical compositions described above.

Other features or advantages of the present invention will be apparent from the following detailed description of several embodiments, and also from the appending claims.

DETAILED DESCRIPTION

A steroid derivative of this invention can be prepared by forming an amide bond between a steroid having a C17 carboxyl-containing substituent and an amino-containing compound or between a steroid having a C17 amino-containing substituent and a carboxyl-containing compound. Similarly, an ester bond can be formed between a steroid with a C17 carboxyl-containing substituent and a hydroxyl-containing compound, or between a steroid with a C17 hydroxyl-containing substituent and a carboxyl-containing compound. Some examples of a steroid that can be used as a starting material are cholic acid (e.g., ursodeoxycholic acid, hyocholic acid, and hyodeoxycholic acid), androstan-17-carboxylic acid (e.g., androstan-3-oxo-17-carboxylic acid and d5-androsten-3-ol-17-carboxylic acid) and pregnan-20-ol (e.g., d5-pregnen-3,17-diol or pregnan-17-ol-3-one). Synthesis of these steroids can be found in the literature, e.g., Roda A. et al., *F. Lipid Res.* vol. 35, pages 2268–2279 (1994) and Roda A. et al., *Dig. Dis. Sci.* vol. 34, pages 24S–35S (1987). Some examples of compounds that can be used to couple to a steroid to form a steroid derivative of this invention are aniline, glycine, phenylalanine, or benzoic acid. Examples of a coupling reagent that can be used in the amide- or ester-forming reaction include 1-ethyl-3-[3-dimethylaminopropyl]-carbodiimide (EDC), dicyclohexyl-carbodiimide (DCC), N-hydroxybenzotriazole (HOBt), 2-(1H-benzotriazole-1-yl)-1,1,3,3-tetramethyluronium hexafluoro-phosphate (HBTU), or benzotriazole-1-yl-oxy-tris-pyrrolidino-phosphonium hexafluorophosphate (PyBOP). The amide- or ester-forming reaction can take place in any solvents that are suitable with the starting materials and reagents. Note that if the reaction takes place in an aqueous solvent, e.g., a buffered solution (or in combination with other miscible organic solvents such as alcohol), isolation of the steroid product for in vitro or in vivo screening assays is not necessary, as the product is already in suitable assaying conditions, i.e., in an aqueous buffered medium. Protection of functional groups, e.g., hydroxyl or keto, on the steroids is not needed. See, e.g., Example 1 below. Due to the simplicity of the reaction, it can be easily automated. Isolation and quantification of the product can be done by thin-layer chromatography, high pressure liquid chromatography, gas chromatography, capillary electrophoresis, or other analytical and preparative procedures. Trifluoromethyl- and taurine-conjugated steroid derivatives can be prepared according to methods described in Li, S. et al., Chem. Phys. Lipids 99:33–71 (1999) and Kurosawa, T. et al., Steroids, 60:439–444 (1995), respectively. As to the preparation of 3β-hydroxy-5-cholesten-25 (R)-26-carboxylic acid derivatives, see Kim, H. et al., J. Lipid Res. 30:247 (1989) and Varma, R. K. et al., J. Org. Chem. 40:3680 (1975). Steroid derivatives having a side chain that contains a double bond, e.g., between C24 and C25, can be prepared according to the following scheme:

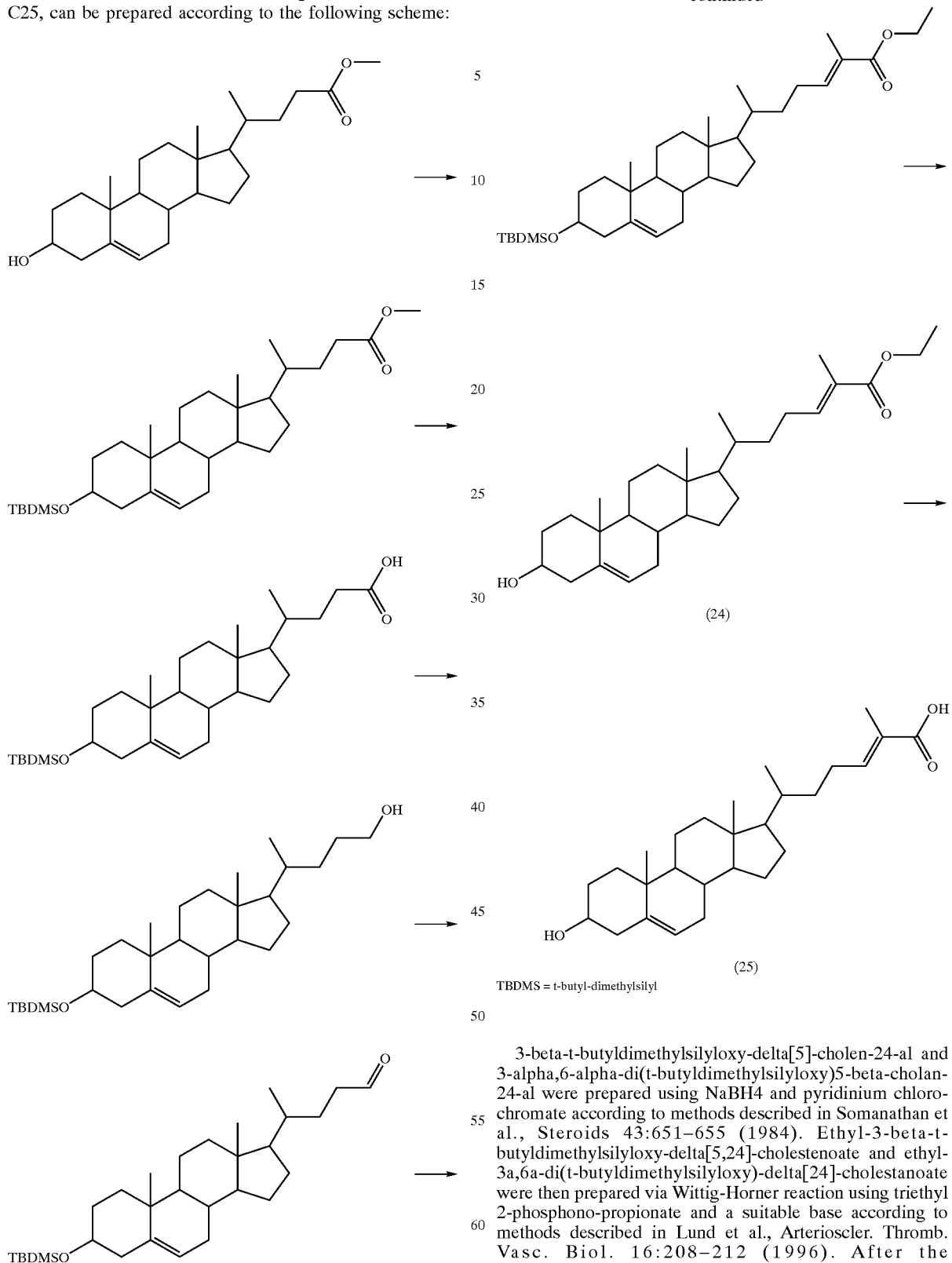

TBDMS = t-butyl-dimethylsilyl 3-beta-t-butyldimethylsilyloxy-delta[5]-cholen-24-al and 3-alpha,6-alpha-di(t-butyldimethylsilyloxy)5-beta-cholan-24-al were prepared using NaBH4 and pyridinium chlorochromate according to methods described in Somanathan et al., Steroids 43:651–655 (1984). Ethyl-3-beta-t-butyldimethylsilyloxy-delta[5,24]-cholestenoate and ethyl-3a,6a-di(t-butyldimethylsilyloxy)-delta[24]-cholestanoate were then prepared via Wittig-Horner reaction using triethyl 2-phosphono-propionate and a suitable base according to methods described in Lund et al., Arterioscler. Thromb. Vasc. Biol. 16:208–212 (1996). After the t-butyldimethylsilyloxyl groups were removed, ethyl ester groups were hydrolyzed under alkaline conditions.

As mentioned above, a pharmaceutical composition containing a steroid derivative or a salt of this invention in an effective amount can be used to treat UR- or LXRa-mediated disorders. Also within the scope of this invention is a method of treating a UR- or LXRa-mediated disorder such as astherosclerosis by administering to a patient such a composition. An effective amount is defined as the amount of the derivative which, upon administration to a patient in need, confers a therapeutic effect on the treated patient. The effective amount to be administered to a patient is typically based on body surface area, patient weight, and patient condition. The interrelationship of dosages for patients (based on milligrams per meter squared of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, N.Y., 1970, 537. An effective amount of a compound of this invention used to practice the invention can range from about 1 mg/kg to about 2 g/kg, e.g., from about 1 mg/kg to about 1 g/kg, or from about 1 mg/kg to about 500 mg/kg. Effective doses will also vary, as recognized by those skilled in the art, dependant on route of administration, excipient usage, and the possibility of co-usage with other therapeutic treatments.

The pharmaceutical composition may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds.

The steroid derivatives of this invention can also be formulated into dosage forms for other routes of administration utilizing well-known methods. They can be formulated, for example, in dosage forms for oral administration in a gel seal, a syrup, a capsule, or a tablet. Capsules may comprise any well-known pharmaceutically acceptable material such as gelatin or cellulose derivatives. Tablets may be formulated in accordance with the conventional procedure by compressing mixtures of the compound of this invention and a solid carrier, and a lubricant. Examples of solid carriers include starch and sugar bentonite. The steroid derivatives of this invention can also be administered in a form of a hard shell tablet or a capsule containing a binder (e.g., lactose or mannitol) and a conventional filler.

The level of interaction between the UR or LXRa protein and a steroid derivative of this invention can be preliminarily evaluated using various assays as described below:

Protease protection assay is a simple assay for measuring the level of interaction between a test steroid and the UR or LXRa protein. This assay can be done by using a $^{35}$S-Met radiolabeled rat UR or human LXRa protein. The radiolabeled protein is then incubated with the steroid of this invention and digested with a protease, e.g., trypsin. A control experiment is done by incubating UR receptor with a protease but without the steroid. Protein fragments from both assays are electrophoresed on a polyacrylamide gel. The fragments from each of the assays can be visualized by exposing the gel to X-ray films and compared side-by-side. A test steroid, if binds to the UR or LXRa protein, will protect the receptor from being digested by the protease. As a result, reactions that result in binding between the steroid and UR will lead to fewer bands of low molecular weights than those that do not result in binding between the two molecules.

The co-activator binding assay employs a fusion protein formed between a glutathione S-transferase (GST) and a co-activator of UR, e.g., Grip1. The GST moiety of the fusion protein binds to a glutathione-coated solid support, thereby immobilizing the fusion protein. UR and a steroid of this invention are then incubated with the immobilized fusion protein. Subsequently, any bound UR is released and collected from the solid support. The proteins are then electrophoresed on a polyacrylamide gel and visualized by exposing the gel to X-ray films. If the steroid interacts with UR, less UR will bind to the fusion protein, and a lighter band would therefore result on the gel. By monitoring the intensity of the band of the bound UR, one can estimate the binding of the steroid to UR.

Yeast two-hybrid binding assay is a sensitive assay for identifying UR modulating compounds by monitoring transcriptional activation. General descriptions of these assay can be found in, e.g., Chien C. T. et al., *Proc. Natl. Acad. Sci. USA*, vol. 88, 9578–9582 (1991); Fields, S. et al., *Nature*, vol. 340, 245–247 (1989); and Green, M. B. et al., *Curr. Biol.*, vol. 2, 403–405 (1992). In this screening method, a steroid of this invention that modulates the interaction of UR or LXRa with its natural ligand will have an effect on the transcriptional activation of a reporter gene. In a specific assay, two plasmids are introduced into a yeast cell. One expresses a fusion protein having a GAL4 DNA binding domain and a UR natural ligand, and the other expresses a fusion protein containing a UR ligand binding domain and a GAL4 activation domain. If the steroid interacts with UR and disrupts the binding of UR to its natural ligand, the activity of the reporting gene (Gal4) will be altered. The changes in reporter activities (i.e., β-galactosidase activities) can be measured with a commercial luminescence kit.

Mammalian cell transfection can also be used to screen steroid derivatives that affect the interaction between the UR protein and a steroid of this invention. A rat UR or human LXR gene and a human RXRa gene are cloned into a mammalian expression vector (e.g., pSG5 from Strategene) and overexpressed. A heterologous promoter is formed by inserting four tandem repeats of a hormone response element $DR^4$ into the vector upstream to a c-fos promoter sequence, which is followed by a sequence encoding luciferase. The entire construct is named $DR^4$-fos-luc. $DR^4$-fos-luc is then co-transfected with pSG5/rUR or CMV/hLXR and pSG5/hRXRa into mammalian cells, e.g., COS-1 cells. An ethanol solution containing a steroid of this invention is then added to the transfected cells. The steroid, if interacts to the UR or LXRa protein, affects the level at which the luciferase gene is activated. The cells are then lysed and assayed for luciferase activity with a commercial assay kit and a luminometer. A high intensity of luminescence indicates that the steroid is a potent UR or LXR agonist.

Another chimeric receptor that can be used in this assay is constructed by fusing oligonucleotides encoding the ligand-binding domain of rat UR to a human AR gene lacking ligand-binding site coding region. For this chimeric receptor, a reporter gene ARE-fos-luc is constructed by inserting three tandem repeats of Androgen Response Element (ARE) into the vector upstream to a c-fos promoter which is followed by a luciferase reporter gene. After adding a steroid of this invention to the medium of the transfected cells, the steroid can interact with UR and affect the level of activation of ARE-fos-luc in cultured cells. The level of luminescence activity thus indicates the level of UR modulation by the steroid.

Yet another assay involves expressing rUR gene in PC-3 cells by retroviral infection. See Underwood et al., *J. Biol. Chem.*, vol. 273, pages 4266–4274 (1998). The transfected cells are then seeded in media containing delipidated serum and then treated with a solution containing a steroid of this invention. The PC-3 cells are later washed with phosphate buffered saline (PBS) and treated with 100 mg/ml amphotericin B in DMEM media without serum at 37EC. Amphotericin B functions to kill cells containing cholesterol in the cell membrane. The cells are then fixed in 10% TCA and stained with Sulforhodamine B after more washing. Viable cells are stained and can then be assessed using a colorimetric assay. The amount of dye is directly proportional to number of surviving cells on the culture plates. From comparing the number of viable cells between assays with and without a steroid, one can estimate the effect the steroid has on the de novo synthesis of cholesterol.

A still further assay makes use of nitrogen monoxide (NO) as an indicator of the level of inflammation. Cells from a murine macrophage cell line RAW264.7 are incubated with a steroid of this invention for 24 hours. The macrophages are then activated by adding lipopolysaccharide (LPS) and gamma-interferon. The NO production of activated macrophages can be monitored indirectly by quantifying NO2 in the media according to Green L. et al., *Anal. Biochem.*, vol. 126, 131–138 (1982). The reduced amount of NO in comparison to that of a control experiment in which no steroid is used indicates that the steroid used in the assay has inhibitory effect on inflammation.

Using the same murine macrophage cell line RAW264.7, constitutive expression of rat UR and human RXRa gene by retroviral systems transforms these cells into foam-cell-like morphology and integrated into clumps while increasing cell sizes and undergo apoptosis. Foam cells originated from macrophages are the major components in pathological plaque which is usually found on the inner wall of blood vessels in patients suffering from atherosclerosis. Steroid derivatives of this invention which modulate UR can suppress the progression of macrophage-foam cell transformation at different stages, and can be used in the treatment or prevention of atherosclerosis. See Kellner-Weibel et al., *Arterioscler. Thromb. Vasc. Biol.*, vol. 18, pages 423–431 (1998).

Yet another assay measures the effect of a steroid of this invention has on the level of adipocyte differentiation on fibroblasts. Specifically, the level of adipocyte differentiation in murine fibroblasts 3T3-L1 containing rat UR gene at sub-confluent conditions is measured. Constitutive expression of rat UR gene in murine fibroblasts 3T3-L1 can be done by using retroviral systems. Full-length rat UR cDNA are inserted into retroviral expression vector MV7. Infected 3T3-L1 cells that are G418-resistant are treated with insulin, dexamethacine, and 1-methyl-3-isobutylxanthine (MIX) to induce adipocyte differentiation. A control experiment can be done by inserting human UR cDNA into MV7 in the antisense orientation. Cells infected with hUR-antisense constructs and parent 3T3-L1 cells are also treated with the same insulin cocktail under same cell density. Cells infected with rUR are shown to accumulate more Red oil O positive lipid drops than parent cells, while cells infected with hUR antisense are shown to have less Red oil O positive lipid drops. Thus, the finding shows that the expression of UR in fibroblasts plays a role in adipocyte differentiation.

Without further elaboration, it is believed that one skilled in the art can, based on the description herein, utilize the present invention to its fullest extent. The following specific examples, which described syntheses, screenings, and biological testings of various compounds of this invention, are therefore, to be construed as merely illustrative, and not limitative of the remainder of the disclosure in any way whatsoever. All publications recited herein, including patents, are hereby incorporated by reference in their entirety.

Preparation of Phenylalanine Conjugated-steroid Derivatives

To a stirred solution of L-(or D-)phenylalanine ester hydrochloride (2 mmol) in dry DMF (10 mL) was added triethylamine (2 mmol) and the mixture was stirred at room temperature for 10 minutes. Bile acid (1 mmol) and 1-ethyl-3-[3-dimethylaminopropyl]-carbodiimide (2 mmol) were then added and the suspension was stirred at room temperature overnight. The reaction mixture was diluted with water and ethyl acetate. The organic layer was separated and the water layer was extracted with ethyl acetate again. The combined organic layer was then washed with 1N HCl water, 1N NaOH and water, and dried (MgSO$_4$). The solvent was removed under reduced pressure to afford the steroid derivatives which were then analyzed by Thin Layer Chromatography, High Pressure Liquid Chromatography, and/or proton-NMR.

Preparation of ethyl-3-alpha,6-alpha-dihydroxy-delta[24]-5-beta-cholestanoate

Ethyl-3-alpha,6-alpha-dihydroxy-delta[24]-5-beta-cholestanoate was prepared according to methods described above. $^1$H NMR: 0.63 (C18); 0.90 (C19); 1.29 (C21); 1.88 (C26); 3.61 (C3); 4.04 (C6); 4.22 (C28); 5.88 (C24).

Preparation of 3-alpha,6-alpha-dihydroxy-delta[24]-5-beta-cholestan-27-oic acid 3-Alpha,6-alpha-dihydroxy-delta[24]-5-beta-cholestan-27-oic acid was prepared according to methods described above. $^1$H NMR: 0.63 (C18); 0.90 (C19); 1.29 (C21); 1.88 (C26); 3.61 (C3); 4.04 (C6); 4.22 (C28); 6.85 (C24).

Preparation of ethyl-3-beta-hydroxy-delta[5,24]-cholestenoate

Ethyl-3-alpha,6-alpha-dihydroxy-delta[24]-5-beta-cholestanoate was prepared according to methods described above. $^1$H NMR: 0.68 (C18); 0.95, 1.00 (C19, C21); 1.83 (C26); 3.50 (C3); 4.19 (C28); 5.34 (C5); 6.74 (C24); $^{13}$C NMR: 72.0 (C3); 121.9 (C5); 143.3 (C6); 168.8 (C27); 127.8, 141.2, 144.0 (C24, C25).

Preparation of 3-beta-hydroxy-delta[5,24]-cholesten-27-oic acid

3-Alpha,6-alpha-dihydroxy-delta[24]-5-beta-cholestan-27-oic acid was prepared according to methods described above. 1H NMR: 0.68 (C18); 0.95, 1.00 (C19, C21); 1.83 (C26); 3.50 (C3); 4.19 (C28); 5.34 (C5); 6.79 (C24).

Yeast Two-hybrid Binding Assay

A commercial yeast two-hybrid kit from Stratagene, HybriZAP-2.1™, was used to construct primary screening system. Four pairs of degenerated oligonucleotides were annealed, digested with EcoRI and SalI, and purified. The sequences of the four pairs of oligonucleotides are listed as follows (N represents A, G, T or C):

> WB1: 5'-GTA TCG CCG GAA TTC NNN TTG NNN NNN TTG TTG NNN NNN TAA GTC GAC TCT AGA GCC-3'
> (SEQ ID NO: 2)
> WB2: 5'-GGC TCT AGA GTC GAC TTA NNN NNN CAA CAA NNN NNN CAA NNN GAA TTC CGG CGA TAC-3'
> (SEQ ID NO: 3)
> LS1: 5'-GTA TCG CCG GAA TTC ATC TTG CAC AGA TTG TTG CAA GAA TAA GTC GAC TCT AGA GCC-3'
> (SEQ ID NO: 4)
> LS2: 5'-GGC TCT AGA GTC GAC TTA TTC TTG CAA CAA TCT GTG CAA GAT GAA TTC CGG CGA TAC-3'
> (SEQ ID NO: 5)
> WD1: 5'-GTA TCG CCG GAA TTC NNN TTG NNN NNN TGG TTG TTG NNN NNN TAA GTC GAC TCT AGA GCC-3'
> (SEQ ID NO: 6)
> WD2: 5'-GGC TCT AGA GTC GAC TTA NNN NNN CAA CAA CCA NNN NNN CAA NNN GAA TTC CGG CGA TAC-3'
> (SEQ ID NO: 7)

The purified fragments were cloned into the yeast vector pBD-GAL4 (Strategene) of the same restriction sites. The resulting plasmid pCAM/BDs expressed a fusion protein with a GAL4 DNA-binding domain (amino acid 1–147 of Gal4) and a polypeptide of ten amino acid in length with a LXXLL (SEQ ID NO: 8) or LXXWLL (SEQ ID NO: 9) motif. UR ligand binding domain (amino acids 141 to 443 of rUR) was generated with PCR and inserted into another yeast vector pAD-GAL4-2.1 (Strategene) with cloning site EcoRI and XhoI. The resulting plasmid, p2.1/rURLB, expressed a fusion protein containing a Gal4 transcription activation domain (amino acids 761–881 of Gal4) and a rUR ligand binding domain.

Plasmids pCAM/BDs and p2.1/rURLB were co-transformed into an appropriate yeast strain by using lithium acetate and polyethylene glycol. The yeast was then grown on selective medium until the formed yeast colonies reached 2 mm. Colonies were picked and grown in selective medium for 15 hours at 30° C. and β-galactosidase activities were measured with a commercial luminescence kit.

Mammalian Cell Transfection Assay (1)

Rat UR and human RXRa gene were cloned into a mammalian expression vector pSG5 (Strategene) by transfection with calcium phosphate and overexpressed in cultured cells. A heterogeneous promoter was constructed by inserting into the vector four tandem repeats of $DR^4$ with sequence 5'-TTC AGG TCA CAG GAG GTC AGA GAG CT-3' (SEQ ID NO: 10) upstream to a c-fos promoter sequence (−56−+109) which was followed by a sequence encoding luciferase. The entire construct was named $DR^4$-fos-luc. $DR^4$-fos-luc was then co-transfected with pSG5/rUR and pSG5/hRXRa into COS-1 cells. 16–24 hours after transfection, a steroid derivative in ethanol was added to the medium until the maximum final concentration is 2 μM. The final concentration of solvent ethanol is 0.2%. After 24–48 hours, cells that were treated with the steroid were lysed and assayed for luciferase activity with a commercial assay kit and a luminometer.

A wide variety of compounds of this invention were tested and found to modulate transactivation activity of UR or LXRa. For example, steroid (1) (see page 5, supra), unexpectedly increased the luciferase activity by 15-fold in comparison to absence of steroid only for UR but not LXRa; steroid (2) unexpectedly increased the luciferase activity by 60-fold in comparison to absence of steroid only for LXRa but not UR; steroid (3), (5) or (10) can activate both UR or LXRa; steroid (7), (8), or (9) can antagonize UR or LXRa transactivation activity.

Mammalian Cell Transfection Assay (2)

In a similar fashion to the experiment described above, another chimeric receptor was constructed by fusing oligonucleotides encoding the ligand-binding domain of rat UR (141 to 443 amino acid residues) to a human AR gene lacking ligand-binding coding region (human AR 1 to 623 amino acid residues) and overexpressed in cultured cells. For this chimeric receptor, a reporter gene ARE-fos-luc was constructed by inserting into the vector three tandem repeats of Androgen Response Element (ARE) with a sequence 5'-TCG AGT CTG GTA CAG GGT GTT CTT TTG-3' (SEQ ID NO: 11) upstream to a c-fos promoter sequence (−56−+109) which was followed by a sequence encoding luciferase.

Various steroid derivatives of this invention were found to modulate UR transactivation activity on $DR^4$-fos-luc expression in the cultured cells. For example, steroid derivative (6) (see page 6, supra) unexpectedly increased the luciferase activity by 5-fold in comparison to the steroid starting material.

Mammalian Cell Transfection Assay (3)

Human embryonic kidney 293 cells were seeded into 48-well culture plates at 105 cells per well in DMEM supplemented with 10% fetal bovine serum. After 24 hours, cells were transfected by a calcium phosphate coprecipitation method with 250 ng of the pGL3/UREluc reporter gene which consists of three copies of AGGTCAagccAGGTCA fused to nucleotides −56 to +109 of the human c-fos promoter in front of the firefly luciferase gene in the plasmid basic pGL3 (Promega), 40 ng pSG5/hRXRa, 40 ng pSG5/rUR or CMX/hLXR, 10 ng pSG5/hGrip1, 0.4 ng CMV/R-luc (transfection normalization reporter, Promega) and 250 ng carrier DNA per well. Alternatively, 500 ng of the pGL2/7aluc reporter gene which consists of a single copy of nucleotides −101 to −49 of the rat 7a-hydroxylase gene fused to the SV40 promoter in front of the firefly luciferase gene in the plasmid basic pGL2 (Promega) was used instead of pGL3/UREluc. This reporter does not have response elements for COUP-TFII or HNF4. In some experiments, 500 ng of the human 7α-hydroxylase gene reporter, PH/hCYP7A-135, which consists of a single copy of nucleotides −135 to +24 of the human CYP7A gene fused to the firefly luciferase gene in the plamid basic pGL3 (Promega), was used instead of pGL2/7aluc. After another 12–24 hours, cells were washed with PBS and refed with DMEM supplemented with 4% delipidated fetal bovine serum. Steroid derivatives dissolved in ethanol were added in duplicate to the medium so that the final concentration of alcohol was 0.2%. After 24–48 hours, cells were harvested and luciferase activity was measured with a commercial kit (Promega Dual luciferase II) on a Monolight luminometer (Beckton Dickenson). Both LXR and UR form heterodimers with RXR for gene transactivation. The ligand for RXR, 9-cis retinoic acid, is known to activate the LXR/RXR heterodimer but addition of 9-cis retinoic acid to transactivation assays did not change the potency of either $\Delta^5$ or 6α-hydroxy steroids for activation of LXR or UR (data not shown). The expression of endogenous LXR and UR (and TR which also binds to a DR4 response element) were apparently low since reporter activation was low in the absence of added expression vectors for LXR or UR. Reporter activation was also low when the DR4 response-element was replaced with a glucocorticoid receptor response element. Each experiment was repeated as least twice to demonstrate reproducability. Relative light units were about $2 \times 10^7$ for pGL3JUREluc, $1 \times 10^6$ for pGL2/7aluc, $5 \times 10^4$ for PH/hCYP7A-135 and $5 \times 10^5$ for CMV/R-luc. Purity of synthesized steroid derivatives was verified by thin layer chromatography and structures were confirmed using proton and $C^{13}$ magnetic resonance spectrometry. 3-Oxo-6α-hydroxy-5β-cholanoic acid methyl ester, 3α,6α-dihydroxy-5β-cholanoic acid methyl ester, and 3α,6α,7α-trihydroxy-5β-cholanoic acid methyl ester were found to be as potent as 3β-hydroxy-$\Delta^5$-cholanoic acid methyl ester as activators for LXR, with $ED_{50}$'s of about 150 nM. Loss of activity was seen when the 6α-hydroxy group was changed to a 6β configuration. In contrast to activity with LXR, 3β-hydroxy-$\Delta^5$- cholanoic acid methyl ester ($ED_{50}$ of 130 nM) was more active than 3-oxo-6α-hydroxy-cholanoic acid methyl ester ($ED_{50}$ of 550 nM) and 3α,6α-dihydroxy-cholanoic acid methyl ester ($ED_{50}$ of 500 nM) for UR activation.

Using the same assay, $ED_{50}$'s of 6α-hydroxylated steroids with 24-keto side chains include free and conjugated 3α,6α-dihydroxy-5β-cholanoic acid and 3α,6α,7α-trihydroxy-5β-cholanoic acid were determined. These steroid derivatives were found to be more selective activators of LXR than UR. 3α,6α-dihydroxy-5β-cholanoic acid activated LXR with an $ED_{50}$ of 17 mM for the free acid and 3 mM for its taurine conjugate. Free and taurine-conjugated 3α,6α-dihydroxy-5β-cholanoic acids activated UR with $ED_{50}$ of 55 mM and 11 mM, values three to four times higher than those for LXR. Cholanoic acid derivatives containing trifluoromethyl moiety were also found to be selective activators of LXR.

The ability of taurine-conjugated 3α,6α-dihydroxy-5β-cholanoic acid to activate LXR using the natural response element derived from the rat 7a-hydroxylase promoter was also investigated. It was found that taurine-conjugated 3α,6α-dihydroxy-5β-cholanoic acid activated LXR but not UR using this reporter gene, with an $ED_{50}$ of 10 mM. To investigate if LXR can activate human CYP7A gene transcription, a chimeric reporter plasmid, in which the nucleotides −135 to +24 of the human CYP7A promoter were fused to the luciferase gene, was used in a co-transfection assay in human embryonic kidney 293 cells along with LXR, RXR and Grip1 expression plasmids. It was found that LXR can activate reporter gene expression in the presence of taurine-conjugated 3α,6α-dihydroxy-5β-cholanoic acid. Taurine-conjugated 3α,7α-dihydroxy-5β-cholanoic acid, on the other hand, suppressed reporter gene expression. Another compound, 3β-hydroxy-5-cholesten-25(R)-26-carboxylic acid activated LXR with an $ED_{50}$ of 300 nNM and UR with an $ED_{50}$ of over 2 µM. Its taurine-conjugated counterpart was also found to be able to trans-activate both LXR and UR. On the other hand, many of its related metabolites were found to be inactive on either receptors.

Protease Protection Assay

Rat UR protein radio-labeled with $^{35}$S-Met is produced with a commercial kit in an in vitro system. The radio-labeled protein is incubated with steroid derivatives with final concentration of up to 1 mM for 2 hours on ice, and digested with trypsin for 30 minutes at 37° C. for 20 minutes. The protected fragments were separated from free $^{35}$S-Met by polyacrylamide electrophoresis and visualized by exposing dried gels to X-ray films.

The patterns of the X-ray film indicate that steroid derivatives of this invention bind to and protect UR from being digested by trypsin. Some examples of such a steroid derivative include 5β-androstan-3a,7b-diol, 5β-androstan-3a-ol-16-one, $\Delta^5$-Pregnen-3b-ol-20-one, 5a-androstan-3-one, 5α-androstan-17-ol-3-one, 5a-androstan-3b-ol-17-carboxylic acid, 5a-pregnan-3,20-dione, and $\Delta^5$-androsten-3b,17b-diol.

Incubation of UR with increasing concentrations of trypsin in the absence of 3α,6α-dihydroxy-5β-cholanoic acid methyl ester leads to extensive digestion of the receptor. In contrast, when UR was incubated with 5 mM 3α,6α-dihydroxy-5β-cholanoic acid methyl ester, two protease-resistant fragments of 35 and 26 kDa were observed. A similar protected pattern was observed with taurine-conjugated 3α,6α-dihydroxy-5β-cholanoic acid.

Co-activator Binding Assay

A fusion protein formed between glutathione S-transferase and Grip1 (termed GST-Grip1) was expressed in E. Coli. The bacteria was lysed by sonication in the presence of detergent NP40 0.1% and Tween-20 0.5%. Soluble GST-Grip1 was separated from insoluble debris by centrifugation at 50,000 G at 4° C. for 30 minutes. The soluble fusion protein was then immobilized to glutathione-agarose. Radiolabeled rat UR protein was incubated with GST-Grip1 coated glutathione-agarose in the presence of a test compound of this invention for 2 hours at 22° C. under agitation. UR that did not bind to the agarose was washed away. Bound UR was eluted with solution containing SDS and β-mercaptoethanol and separated from free $^{35}$S-Met with polyacrylamide electrophoresis, and finally visualized by exposure the dried gel to X-ray films. Diosgenin was shown to be capable of promoting UR and Grip 1 protein interaction in this assay.

Another fusion protein GST-rUR was expressed in E. Coli strain BL21 using the expression plasmid pGEX using a method similar to that as described above. Transfected cells were lysed by one cycle of freeze-thaw and sonication. Supernatant, prepared by centrifugation at 45,000 G for 1 hour, was incubated with glutathione-agarose for 10 min at 4° C. The agarose was washed with binding buffer (20 mM Hepes, pH7.5, 10 mM EDTA, 10 mM $Na_2MoO_4$, 1 mM β-mercaptoethanol, 1 mM DTT, 0.5 mM PMSF, 2 ug/ml aprotinin). Human Grip1 was produced by in vitro translation using a rabbit reticulocyte lysate and labeled with [$^{35}$S]-methionine. [$^{5}$]-Grip1 in reticulate lysate (2 ml) was added to GST-UR bound to agarose beads in 100 ul binding buffer. Test chemicals in ethanol were added to the mixture and the slurry was shaken at room temperature for 30 min. The agarose beads were then washed three times with binding buffer. Bound protein was eluted with SDS-PAGE loading buffer and separated on a 8% SDS-PAGE gel. Gels were dried and subjected to autoradiography. Radioactive Grip1 was measured with a STORM phosphoimager (Molecular Dynamics).

Both 3α,6α-dihydroxy-5β-cholanoic acid methyl ester and 22R-hydroxy cholesterol promoted interaction of Grip1 with GST-UR and taurine-conjugated 3α,6α-dihydroxy-5β-cholanoic acid promoted interaction of Grip1 with GST-LXR. Taurine-conjugated 3α-hydroxy-5β-cholanoic acid, taurine-conjugated 3α-hydroxy-5β-cholanoic acid, and taurine-conjugated 3α,7α-dihydroxy-5β-cholanoic acid all failed to enhance coactivator-receptor interaction under the same conditions.

Using the same conditions, 3β-hydroxy-5-cholesten-25(R)-26-carboxylic acid was found to bind to and form complexes with LXR and nuclear receptor co-activator Grip 1, indicating that this acid bound to LXR and induced a conformation change that favored co-activator binding. In a dose response analysis, 3β-hydroxy-5-cholesten-25(R)-26-carboxylic acid increased the amount of [$^{35}$S]-Grip1 bound to LXR with an $EC_{50}$ value of 300 nM, which correlates with the cell-based transfection assay. These data showed that 3β-hydroxy-5-cholesten-25(R)-26-carboxylic acid is a LXR agonist.

Inhibition of de novo Cholesterol Synthesis in Cultured Cells

On day 1, PC-3 cells stably expressing rUR gene by retroviral infection were seeded in media containing delipidated serum. On day 2, cells were treated with an ethanol solution containing a test compound at maximum concentration of 2 µM. On day 3, cells were washed with PBS and treated with 100 mg/ml amphotericin B in Dulbecco's Modified Eagle Medium (DMEM) without serum at 37□C. 4 hours later, cells were then washed and treated with solution containing 80% water and 20% DMEM for 30 minutes. Surviving cells were assessed using a colorimetric assay. Cells were fixed in 10% trichloroacetic acid (TCA) and stained with sulforhodamine B. The amount of dye is linear to number of fixed cells on the culture plates. Cells with cholesterol in the cell membrane were killed by amphotericin B treatment.

Compounds of this invention were found to inhibit cholesterol synthesis of the cell to various extent.

Measuring the Level of Inflammation in Cells by Monitoring the Amount of $NO_2$

Murine macrophage cell line RAW264.7 were incubated with a test compound at maximum final concentration of 2 µM for 24 hours. The macrophages were then activated by adding lipopolysaccharide (100 ng/mL) and γ-interferon (100 units/mL). The nitrogen monoxide (NO) production of activated macrophages was measured indirectly by quantifying nitrogen dioxide ($NO_2$) in the media according to Green L. et al., Anal. Biochem. 126, 131–138 (1982). Compounds of this invention were found to inhibit cholesterol synthesis of the cell to various extent.

Macrophage-foam Cell Transformation

Constitutive expression of rat UR and human RXRa gene by retroviral systems in RAW264.7 transformed these cells into foam-cell-like morphology and integrated into clamps while increasing cell sizes and undergoing apoptosis. Foam cells originated from macrophages are the major components in pathological plaques formed on the inner wall of blood vessels which are a characteristic feature in atherosclerosis. Compounds of this invention were shown to be able to suppress the progression of macrophage-foam cell transformation at different stages, and thus can be used in the treatment or prevention of atherosclerosis.

Adipocyte Differentiation

Constitutive expression of rat UR gene in murine fibroblasts 3T3-L1 was done by using retroviral systems. Full-length rat UR cDNA was inserted into retroviral expression vector MV7. Infected 3T3-L1 cells that are G418-resistant were treated with 5 µg/ml insulin, 250 nM dexamethacine, and 0.5 mM 1-methyl-3-isobutylxanthine (MIX) to induce adipocyte differentiation. A control experiment was done by inserting human UR cDNA into MV7 in the antisense orientation. Cells infected with hUR-antisense constructs and parent 3T3-L1 cells were also treated with the same insulin cocktail under same cell density. Cells infected with rUR were shown to accumulate more Red oil O positive lipid drops than parent cells, while cells infected with hUR antisense were shown to have less Red oil O positive lipid drops.

Erythrocyte Differentiation

Constitutive expression of rat UR gene in murine NN10, IW32.1 or IW201 was done by using retroviral systems. Full-length rat UR cDNA was inserted into retroviral expression vector MV7. Infected cells that were G418-resistant were cultured upto 5 days to induce erythrocyte differentiation. A control experiment was done by using parent MV7 vector. NN10, IW32.1 or IW201 cells infected with parent MV7 construct were also treated with G418 in parallel under same cell density. More cells infected with rUR were shown to accumulate hemoglobin protein (stained with benzidine) than parent or control cells. When IW32.1/rUR cells were cultured on fibronectin-coated plates, some cells differentiated into mature enucleated reticulocytes.

Animal Studies

Male Sprague-Dawley rats that were 50 days old were fed a regular chow diet and tap water ad libitum for 1 week during acclimatization, and then randomly divided into groups that were given different dietary treatments. Both control and treatment groups were initially fed ad libitum a cholesterol-enriched diet, which was prepared by adding 2% cholesterol and 1% 3α,7α,12α-trihydroxy-5β-cholanoic acid to the regular chow diet. The treatment group received the same diet supplemented with 0.03% test steroid derivative. Rats were fasted overnight before determining body and liver weight and drawing blood from the tail vein for serum total cholesterol measurements. Total cholesterol was determined enzymatically with a diagnostic kit (Sigma, St. Louis, Mo.) on day 0 and 7. Average food consumption was 20–25 g/rat/day and average feces production was 9 g/rat/day. There was no statistical difference between control and treatment groups for food consumption and feces production.

The dose for test steroid derivative in the treatment group was 40–50 mg/kg/day. Rats on high cholesterol/bile acid diet and treated with a trifluoromethyl conjugated 3α,6α-dihydroxy-5β-cholanoic acid had a 20% drop (p<0.05) in the serum total cholesterol compared with the level in untreated animals (Table 1). Food consumption, body and liver weight were similar in the control and treatment groups. In another experiement, rats were made hypercholesterolemic with a high cholesterol/cholic acid diet and then treatment with the same trifluoromethyl conjugated 3α,6α-dihydroxy-5β-cholanoic acid again lowered the serum total cholesterol by 20% compared with untreated animals.

Other Embodiments

From the above description, one skilled in the art can easily ascertain the essential characteristics of the present invention, and without departing from the spirit and scope thereof, can make various changes and modifications of the invention to adapt it to various usages and conditions. For example, the moiety A can be a side chain of an amino acid which is structurally similar to a naturally occurring amino acid described above. One specific example of A is a side chain of phenylglycine. Thus, other embodiments are also within the claims.

What is claimed is:

1. A compound of the following formula:

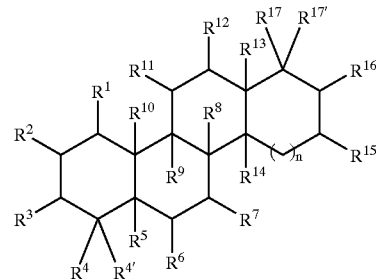

wherein
each of $R^1, R^2, R^4, R^{4'}, R^5, R^7, R^8, R^9, R^{11}, R^{12}, R^{14}, R^{15}, R^{16}$, and $R^{17'}$, independently, is hydrogen;
each of $R^3$ and $R^6$, independently, is hydroxy;
each of $R^{10}$ and $R^{13}$, independently, is alkyl, haloalkyl, or hydroxyalkyl;
$R^{17}$ is —X—Y—Z, in which
X is alkyl or alkenyl;
Y is —CO—NH— or —CO—N(alkyl)-; and
Z is alkynyl, heterocycloalkyl, cycloalkenyl, heterocycloalkenyl, heteroaryl, or heteroaralkyl, and is optionally substituted with hydroxy, alkoxy, halo, oxo, alkylcarbonyloxy, alkylaminocarbonyl, alkylcarbonylamino, alkylcarbonyl, alkylsulfinyl, or alkylthio; is straight chain $C_1$–$C_8$ alkyl, alkenyl, or cycloalkyl, which is substituted with hydroxy, alkoxy, halo, oxo, alkylcarbonyloxy, alkylaminocarbonyl, alkylcarbonylamino, alkylcarbonyl, alkylsulfinyl, or alkylthio; or is —CH(A)—B with A being an amino acid side chain containing an aromatic moiety, and B being hydrogen, —NR$^a$R$^b$, or —COOR$^c$ wherein each of R$^a$, R$^b$, and R$^c$, independently, is hydrogen or alkyl; and
n is 0;
or a salt thereof.

2. The compound of claim 1, wherein each of $R^3$ and $R^6$, independently, is in the α-configuration.

3. The compound of claim 1, wherein $R^5$ is in the β-configuration.

4. The compound of claim 1, wherein X is alkyl.

5. The compound of claim 4, wherein Y is —C(=O)—NH—; and Z is —CH(A)— B with A being a side chain of Tyr or Phe, and B being —NR$^a$R$^b$ or —COOR$^c$.

6. The compound of claim 1, wherein Y is —CO—NH—.

7. The compound of claim 6, wherein Z is straight chain $C_1$–$C_8$ alkyl or alkenyl substituted with hydroxy, alkoxy, halo, or alkylsulfinyl; or is, heteroaryl, or heteroaralkyl, and is optionally substituted with hydroxy, alkoxy, halo, or alkylsulfinyl; or is —CH(A)—B.

8. The compound of claim 1, wherein Z is straight chain $C_1$–$C_8$ alkyl substituted with hydroxy; or is —CH(A)—B with A being an amino acid side chain having an aromatic moiety, and B being —NR$^a$R$^b$, or —COOR$^c$.

9. The compound of claim 1, wherein $R^{17}$ contains a straight chain having 6–20 chain atoms.

10. The compound of claim 9, wherein $R^{17}$ contains a straight chain having 8–16 chain atoms.

11. The compound of claim 1, wherein said compound is:

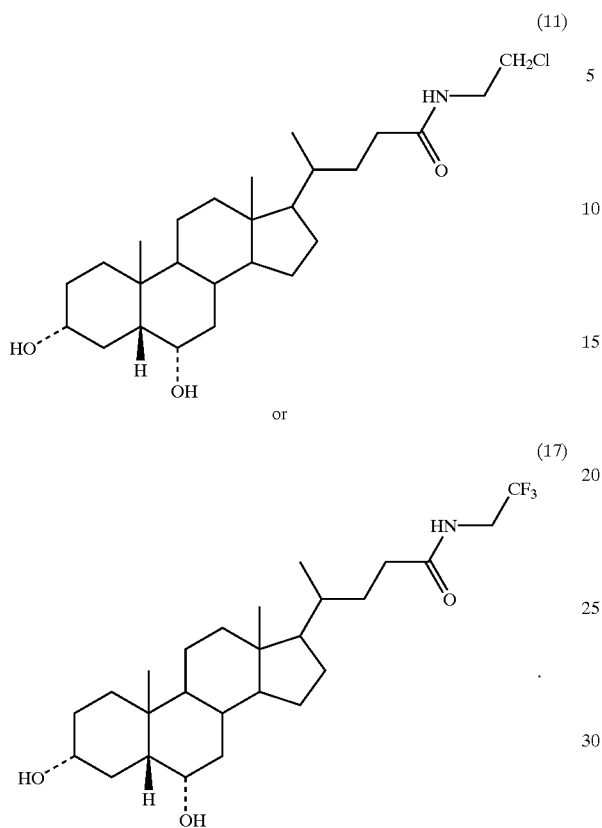

12. A pharmaceutical composition for treating a UR- or a LXR-mediated disorder, said composition comprising a pharmaceutically acceptable carrier and an effective amount of a compound of the following formula:

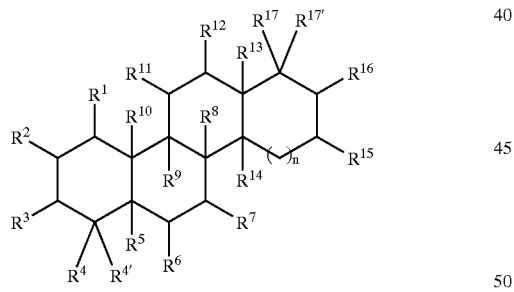

wherein
each of $R^1$, $R^2$, $R^4$, $R^{4'}$, $R^5$, $R^7$, $R^8$, $R^9$, $R^{11}$, $R^{12}$, $R^{14}$, $R^{15}$, $R^{16}$, and $R^{17'}$, independently, is hydrogen;
each of $R^3$ and $R^6$, independently, is hydroxy;
each of $R^{10}$ and $R^{13}$, independently, is alkyl, haloalkyl, or hydroxyalkyl;
$R^{17}$ is —X—Y—Z, in which X is alkyl or alkenyl;
Y is —CO—NH— or —CO—N(alkyl)-; and
Z is alkynyl, heterocycloalkyl, cycloalkenyl, heterocycloalkenyl, heteroaryl, or heteroaralkyl, and is optionally substituted with hydroxy, alkoxy, halo, oxo, alkylcarbonyloxy, alkylaminocarbonyl, alkylcarbonylamino, alkylcarbonyl, alkylsulfinyl, or alkylthio; is straight chain $C_1$–$C_8$ alkyl, alkenyl, or cycloalkyl, which is substituted with hydroxy, alkoxy, halo, oxo, alkylcarbonyloxy, alkylaminocarbonyl, alkylcarbonylamino, alkylcarbonyl, alkylsulfinyl, or alkylthio; or is —CH(A)—B with A being an amino acid side chain containing an aromatic moiety, and B being hydrogen, —$NR^aR^b$, or —$COOR^c$ wherein each of $R^a$, $R^b$, and $R^c$, independently, is hydrogen or alkyl; and n is 0;
or a salt thereof.

13. The composition of claim 12, wherein said compound is:

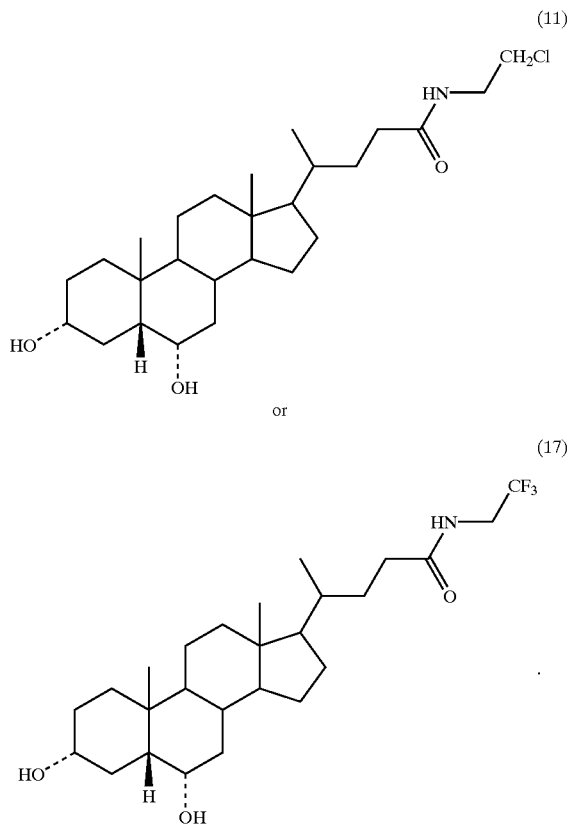

* * * * *